United States Patent [19]

Drehman et al.

[11] 4,049,743
[45] Sept. 20, 1977

[54] SELECTIVE OXIDATION OF ACETYLENES

[75] Inventors: Lewis E. Drehman; Floyd Farha, Jr., both of Bartlesville, Okla.

[73] Assignee: Phillips Petroleum Company, Bartlesville, Okla.

[21] Appl. No.: 703,164

[22] Filed: July 7, 1976

[51] Int. Cl.$^2$ .............................................. C07C 11/02
[52] U.S. Cl. ........................... 260/681.5 R; 260/680 R
[58] Field of Search .............................. 260/681.5, 680

[56] References Cited

U.S. PATENT DOCUMENTS 3,202,727  8/1965  Dancer .............................. 260/681.5
3,823,088  7/1974  Box, Jr. et al. ........................ 210/63

Primary Examiner—Veronica O'Keefe

[57] ABSTRACT

Acetylenic compounds are selectively removed from hydrocarbon mixtures containing same by oxidation in the presence of a copper-manganese-rare earth metal-zinc aluminate catalyst. In one embodiment, acetylenic compounds are selectively removed from a conjugated diene mixture containing same by contacting oxygen and the mixture with a catalyst of zinc aluminate promoted with copper, manganese, and a rare earth metal under oxidizing conditions.

7 Claims, No Drawings

SELECTIVE OXIDATION OF ACETYLENES

This invention relates to the purification of unsaturated hydrocarbon-containing mixtures to remove undesirable contaminants therefrom. In accordance with one aspect, this invention relates to a method of removing unsaturants, such as acetylenes, from hydrocarbon mixtures containing same by contacting the mixture and oxygen at an elevated temperature with a copper-manganese-rare earth metal-zinc aluminate catalyst. In accordance with a further aspect, this invention relates to a process for the purification of conjugated diene-containing mixtures also containing acetylenic compounds as impurities by contacting at an elevated temperature with zinc aluminate promoted with copper manganese and a rare earth metal such as a cerium group rare earth metal under oxidizing conditions. In accordance with a further aspect, this invention relates to a process for the purification of the effluent from an oxidative dehydrogenation process by oxidizing the effluent with a copper-manganese-rare earth metal-zinc aluminate catalyst to selectively remove acetylenic compounds therefrom.

The present invention provides a method whereby acetylenes such as vinylacetylene, methylactylene, 1-butyne, and the like can be selectively removed from hydrocarbon mixtures containing same, especially conjugated diene mixtures containing them, without the necessity for hydrogenation and extensive fractionation. There is thus provided a means whereby substantial reduction and planned investment in utility is realized.

The invention relates more specifically to a process for removing acetylenic compounds (impurities) found in small amounts, i.e., 0.05-1 mole percent in refinery streams comprising paraffins, olefins, diolefins, water, nitrogen, oxygen, etc. The product gas stream obtained by the vapor phase catalytic oxidation of butenes to form butadiene is a typical stream which can be treated by the process of the present invention. Such a gas stream contains, in addition to butadiene, unreacted butene, water, oxygen, nitrogen, carbon dioxide, carbon monoxide, and traces of acetylenes. The presence of acetylenes in the product is most undesirable, causing difficulties in the subsequent separation of butadiene from unreacted butenes and being an unacceptable impurity in the final product.

It has now been found that by selective oxidation in the presence of a copper-manganese-rare earth metal-zinc aluminate catalyst it is possible to remove the acetylenes from such gaseous streams without loss of butadiene by oxidation.

Accordingly, an object of this invention is to provide a simplified process for removing acetylenes from unsaturated hydrocarbon-containing mixtures such as conjugated diene streams.

Another object of this invention is to provide an improved process for removing acetylenes from conjugated diene-containing mixtures to provide a highly purified conjugated diene-containing stream.

A further object of this invention is to provide a process for purification of conjugated diene streams obtained from oxidative dehydrogenation processes whereby acetylenic contaminants are removed therefrom.

Further objects and aspects, as well as the several advantages of this invention, will be apparent to those skilled in the art upon the study of the disclosure and the appended claims.

According to the present invention, a process for the removal of selective oxidation of acetylenic compounds from a gas stream containing same is provided which comprises passing the gas stream in admixture with sufficient oxygen over a copper-manganese-rare earth metal-zinc aluminate catalyst under conditions of temperature and pressure sufficient to remove a substantial portion of the acetylenes present without destroying desirable unsaturated hydrocarbons present in the stream treated.

More specifically, according to this invention, acetylenic compounds in hydrocarbon-containing streams such as butadiene-containing streams are removed by selective oxidation under reaction conditions in the presence of free oxygen by contact with a copper-manganese-rare earth metal-zinc aluminate catalyst.

In actual operation, the acetylenes present in the stream being treated are selectively oxidized to water and carbon oxides in the presence of molecular oxygen by contact with a solid catalyst consisting essentially of zinc aluminate promoted with copper, manganese, and a rare earth metal, preferably at least one cerium subgroup rare earth metal such as lanthanum and cerium. It has been observed that such catalysts exhibit extended catalyst life and improved catalyst stability in that little, if any, promoting metal is lost during actual use.

Generally, the catalysts are preferably prepared by impregnating the zinc aluminate substrate with a solution containing one or more of the promoting metal compounds. It is convenient to include all the metal components in one solution although sequential impregnation can be utilized with a solution containing only one component, if desired. Also, dry mixing of the substrate with solid compounds of the promoter metal compounds can be used in an alternative procedure. Suitable metal compounds employed are preferably those which are convertible to the metal oxide or to the metal when the compositions are calcined. Examples of such compounds include but are not restricted to the carbonates, hydroxides, nitrates, oxalates, and oxides, and the metal salts of such carboxylic acids as acetic, citric, formic, tartaric, and the like. The resulting compositions are dried, if necessary, and calcined in air for about 30 minutes to 20 hours or longer at temperatures ranging from about 500° to 1600° F (260°–871° C), more preferably from about 875° to 1100° F (468°–593° C). The products, after cooling, are generally ground and screened, and utilized in the form of particles ranging in size from about 4 to about 40 mesh based on U.S. Sieve series. If desired, the powdered catalyst can also be formed into pellets, wafers, cylinders, etc., ranging in size from about 1/32 to ½ inch (0.08–1.3 cm) by means of conventional pelleting practices and used in that form. The finished (calcined) catalyst has a surface area ranging from about 5–50 square meters per gram.

The concentration of each promoter metal on the zinc aluminate, after calcination, is generally in the range of 0.1 to 20 weight percent, preferably 1-10 weight percent, calculated as the metals and based on the weight of zinc aluminate plus metal promoters.

The process of the invention can be carried out under a wide range of oxidation conditions, depending upon feedstock, catalysts, and desired degree of acetylenes removal. The reaction can be carried out in any suitable apparatus, either continuously or batchwise. Continuous operation through a fixed catalyst bed is the presently preferred mode of reaction.

Process conditions suitable in practicing the invention include reaction temperatures ranging from about 250°-800° F (121-427° C), more preferably from about 400°-650° F (204°-343° C); reaction pressures ranging from about 0.5-500 psig (3.4-3447 kPa gage), more preferably from about 5-100 psig (34-689 kPa gage); an oxygen to total hydrocarbon mole ratio ranging from about 0.01-0.2, more preferably from about 0.02-0.12; and a steam to total hydrocarbon mole ratio of 0 to about 100, more preferably about 10 to about 50. Hydrocarbon feed rates can range from about 50 to about 5,000 gaseous hourly space velocity (GHSV).

EXAMPLE

Catalyst 1 was prepared by impregnating 125 g of zinc aluminate as 1/32 inch extrudate, commercially obtained, as received with 89 cc of a solution made up as follows:

25.8 cc Cu(NO$_3$)$_2$ solution containing 0.194 g Cu/cc,
10.6 cc 50 wt. % Mn(NO$_3$)$_2$ solution,
12.5 cc La(NO$_3$)$_3$ solution containing 0.1 g La/cc, and
40 cc distilled water.

After soaking, 30 cc of excess solution was drained off. The composition was dried under a heat lamp, then impregnated with the excess solution and redried. The resulting composition was calcined in air for 3 hours at 1050° F (566° C), cooled, ground, and screened to obtain 18-40 mesh particles. The final catalyst as analyzed contained 3.7 wt. percent copper, 1.8 wt. percent manganese, 0.9 wt. percent lanthanum, each calculated as the metal, and 91.8 wt. percent zinc aluminate. Combined oxygen in this catalyst as oxides amounted to 1.8 wt. percent. Apparent bulk density of the catalyst was 1.1 g/cc.

Catalyst 2 was prepared by impregnating 800 g of zinc aluminate as 1/16 inch extrudate commercially obtained and calcined 3 hours in air at 1875° F (1024° C), with 650 cc of a solution made up as follows:

419 g Cu(NO$_3$)$_2$.3H$_2$O,
82.2 g La(NO$_3$)$_3$.5H$_2$O,
233 cc 50 wt. % Mn(NO$_3$)$_2$ solution, and
Distilled water to give a final volume of 1950 cc.

The zinc aluminate was soaked in a 1-liter filter flask under house vacuum for 30 minutes. Atmospheric pressure was reestablished, about 325 cc excess solution decanted, and the solid product was dried under a heat lamp and then calcined in air for 3 hours at 1050° F. The resulting product, after cooling, was reimpregnated with the decanted solution diluted to 400 cc, and the resulting composition was dried under a heat lamp. The product was calcined in air for 4 hours at 1050° F, cooled, ground, and screened to obtain 20-40 mesh particles. The final catalyst as analyzed contained 4.2 weight percent copper, 2.1 weight percent manganese, 1.2 weight percent lanthanum, each calculated as the metal, and 90.5 weight percent zinc aluminate. Combined oxygen in this catalyst as oxides amounted to 2 weight percent. Apparent bulk density of the catalyst was 1.0 g/cc.

Catalyst 3 was prepared by impregnating 800 g of another batch of commercially obtained zinc aluminate as 1/16 inch extrudate and calcined 3 hours in air at 1850° F (1010° C), with 650 cc of a solution made up as follows:

435 g Cu(NO$_3$)$_2$.3H$_2$O,
85 g La(NO$_3$)$_3$.5H$_2$O,
250 cc 50 wt. % Mn(NO$_3$)$_2$ solution, and
Distilled water to give a final volume of 1950 cc.

The zinc aluminate was soaked for one hour in a 1-liter filter flask under house vacuum. Atmospheric pressure was reestablished, about 300 cc of excess solution was filtered off, the solid product was dried under a heat lamp and the composition was calcined in air for 3 hours at 900°-1000° F (482°-538° C). The resulting product, after cooling, was reimpregnated with the filtrate diluted tc 350 cc, the resulting composition was dried under a heat lamp and then in an oven at 120° C. The product was calcined in air for 5 hours at 1550° F (843° C), cooled, ground, and screened to obtained 20-40 mesh particles. The final catalyst, as analyzed, contained 4.7 weight percent copper, 2.1 weight percent manganese, 0.96 weight percent lanthanum, each calculated as the metal, and 90.1 weight percent zinc aluminate. Combined oxygen in this catalyst as oxides amounted to 2.1 weight percent. The surface area of the catalyst was 11.6 square meters/g. Apparent bulk density was 1.03 g/cc.

A hydrocarbon stream such as obtained as the effluent from a butene oxidative dehydrogenation process consisting of 89.03 mole percent butadiene, 0.155 mole percent vinylacetylene, 10.48 mole percent butenes, 0.08 mole percent n-butane, and 0.01 mole percent neopentane was contacted in the presence of air, with a catalyst and in some instances with steam, at a reactor temperature of 600° F (316° C). In each run, 3 cc of the catalyst in the form of about 20-40 mesh particles was charged to a tubular, fixed bed reactor. The conditions employed and results obtained are presented in Table I.

TABLE I

OXIDATION OF VINYLACETYLENE WITH Cu/Mn/La/ZnAl$_2$O$_4$ CATALYSTS

| Run No. | Catalyst Description No | Wt. % Cu | Wt. % Mn | Wt. % La | Catalyst Age (hours) | Test Pressure (psig) | Test Pressure (kPa) | Feed GHSV | Mole Ratios Oxygen/Feed | Mole Ratios Steam/Feed | Conversions, Percent vinylacetylene | Conversions, Percent Butadiene | Conversions, Percent Butenes |
|---|---|---|---|---|---|---|---|---|---|---|---|---|---|
| 1 | 1 | 3.7 | 1.8 | 0.90 | 12.5 | 10 | 68.9 | 1461 | 0.033 | 0 | 87.7 | 0.95 | 1.8 |
| 2 | 1 | 3.7 | 1.8 | 0.90 | 30.0 | 10 | 68.9 | 1127 | 0.032 | 0 | 18.8 | 0.79 | 1.5 |
| 3 | 1 | 3.7 | 1.8 | 0.90 | 8.7[1] | 10 | 68.9 | 1104 | 0.032 | 27.1 | 92.0 | 0.64 | 2.2 |
| 4 | 1 | 3.7 | 1.8 | 0.90 | 24.7 | 10 | 68.9 | 1122 | 0.032 | 18.2 | 74.6 | 0.54 | 1.6 |
| 5 | 2 | 4.2 | 2.1 | 1.2 | 33.0 | 10 | 68.9 | 909 | 0.033 | 0 | 100.0 | 0.78 | 0.34 |
| 6 | 2 | 4.2 | 2.1 | 1.2 | 35.8 | 10 | 68.9 | 932 | 0.030 | 0 | 73.4 | 0.89 | 0.19 |
| 7 | 2 | 4.2 | 2.1 | 1.2 | 51.3 | 10 | 68.9 | 923 | 0.029 | 0 | 38.0 | 1.3 | −0.55[2] |
| 8 | 2 | 4.2 | 2.1 | 1.2 | 56.8 | 10 | 68.9 | 922 | 0.031 | 0 | 100.0[3] | 1.1 | −0.53 |
| 9 | 2 | 4.2 | 2.1 | 1.2 | 60.1 | 10 | 68.9 | 929 | 0.031 | 0 | 39.9 | 1.5 | −0.87 |
| 10 | 2 | 4.2 | 2.1 | 1.2 | 75.4 | 13 | 89.6 | 924 | 0.030 | 21.8 | 100.0 | 1.2 | 1.8 |
| 11 | 3 | 4.7 | 2.1 | 0.96 | 7.5 | 10 | 68.9 | 1148 | 0.033 | 0 | 100.0 | 0.19 | 6.5 |
| 12 | 3 | 4.7 | 2.1 | 0.96 | 87.8 | 11 | 75.8 | 1184 | 0.032 | 17.4 | 100.0 | 0.06 | 6.0 |

Notes:
[1]Fresh catalyst used, stating with Run 3.
[2]Minus sign indicates net formation of butenes.
[3]Catalyst regenerated after terminating Run 7.

As an example of the composition fed to the reactor and the reactor product obtained, the compositions for Run 5 are shown in terms of mole percent:

|  | Charge | Product |
|---|---|---|
| Oxygen | 2.86 | 0.41 |
| Nitrogen | 10.21 | 9.99 |
| Hydrogen | 0.00 | 0.00 |
| Carbon monoxide | 0.00 | 0.10 |
| Carbon dioxide | 0.00 | 1.23 |
| Methane | 0.00 | 0.00 |
| Ethylene | 0.0 | 0.01 |
| Propane | 0.00 | 0.00 |
| Propylene | 0.00 | 0.00 |
| Isobutane | 0.00 | 0.00 |
| n-Butane | 0.07 | 0.07 |
| Neopentane | 0.01 | 0.01 |
| Water | 0.00 | 2.21 |
| Coke (calculated) | 0.00 | 1.75 |
| Butene-1 | 1.24 | 1.24 |
| t-Butene-2 | 2.54 | 2.54 |
| c-Butene-2 | 5.34 | 5.12 |
| Butadiene | 77.40 | 75.15 |
| $C_5$'s | 0.20 | 0.18 |
| Vinylacetylene | 0.135 | 0.000 |

Inspection of the results presented in the Table reveals that all the invention catalysts effectively remove vinylacetylene from the feed without significantly oxidizing butadiene. The catalysts operate in the absence or presence of steam. However, steam appears to be beneficial in the process as a means to not only prolong the effectiveness of the catalyst (higher vinylacetylene oxidation) lower butadiene loss) as runs 3 and 4 show compared to runs 1 and 2, but also to improve the results obtained. In this regard, note run 10, 100% vinylacetylene conversion and 1.2% butadiene conversion as compared to the 39.9% conversion and 1.5% butadiene conversion shown in run 9.

The results obtained in runs 10 and 11 suggest a more stable and long lasting catalyst is obtained when zinc aluminate is calcined at about 1850° F (1010° C) prior to being impregnated with promoter metals.

The results also show in runs 7 and 8, that a catalyst that is losing its ability to remove vinylacetylene can be completely restored in effectiveness to remove 100% of vinylacetylene by regeneration of the spent catalyst. Regeneration is accomplished at reaction temperature by shutting off the feed supply while air and optionally steam continue to contact the catalyst.

The invention is not confined to the treatment of $C_4$ fractions containing butadiene although this is a preferred embodiment. Typical feed streams which can be successfully treated according to the invention include commercial hydrocarbon-containing streams obtained in petroleum refining and cracking operations. Such streams usually contain alkanes of up to about five carbon atoms; olefins such as ethylene, propylene, butylene, and amylene; diolefins such as allene, butadiene, 1,3-dimethylallene, isoprene, and 1,3-pentadiene; and relatively minor amounts of acetylenic compounds such as acetylene, methylacetylene, ethylacetylene, vinylacetylene, etc., as well as some additional hydrocarbons and other organic compounds with more than five carbon atoms. Generally, acetylenic impurities such as those found in streams of corresponding hydrocarbons less highly unsaturated, for example, in streams consisting largely or in some part of the lower olefins and diolefins, are generally treated according to the invention. Of course, the acetylenic hydrocarbon impurities are also removable by the present catalyst from other gases such as air, inert purge gases, and the like.

We claim:

1. A process for the selective removal of acetylenic contaminants or impurities present in hydrocarbon streams which comprises contacting oxygen and a gaseous hydrocarbon stream comprising lower olefins and diolefins contaminated with relatively minor amounts of acetylenic compounds with a catalyst consisting essentially of zinc aluminate promoted with copper, manganese, and a rare earth metal in which each of the promoter metals is present in an amount ranging from about 0.1 to about 20 weight percent based on the weight of zinc aluminate plus metal promoters under oxidation conditions including a temperature and a mole ratio of oxygen to hydrocarbon sufficient to remove a substantial portion of said acetylenic compounds present in said stream without destroying desirable unsaturated hydrocarbons present in the stream treated.

2. A process according to claim 1 wherein said contacting is effected at a temperature in the range of about 250°–800° F (121°–427° C), a reaction pressure in the range of about 0.5–500 psig (3.4–3447 kPa gage), an oxygen to hydrocarbon mole ratio in the range of about 0.01–0.2, and a hydrocarbon feed rate ranging from about 50 to about 5,000 GHSV.

3. A process according to claim 1 wherein said contacting is effected in the presence of steam at a steam to hydrocarbon mole ratio of up to about 100.

4. A process according to claim 1 wherein said contacting is effected in the presence of air and steam at a steam to hydrocarbon mole ratio up to about 100 at a temperature in the range of about 400°–650° F (204°–343° C).

5. A process according to claim 1 wherein said stream is a mixture of unsaturated hydrocarbons obtained as the effluent from the oxidative dehydrogenation of olefins and the effluent contains oxygen, steam, and vinylacetylene, as well as butadiene and other $C_4$ hydrocarbons, and said contacting is effected at a temperature in the range of about 400°–650° F (204°–343° C).

6. A process according to claim 1 wherein zinc aluminate is promoted with about 1–10 wt. % of each of the promoter metals and the contacting is effected in the presence of air and steam at a steam to hydrocarbon mole ratio of about 10 to about 50 at a temperature in the range of about 400°–650° F (204°–343° C).

7. A process according to claim 1 wherein said stream comprises a mixture of unsaturated $C_4$ hydrocarbons including butadiene and said catalyst is zinc aluminate promoted with about 1–10 wt. % of each of copper, manganese, and lanthanum.

* * * * *